(12) United States Patent
Collins et al.

(10) Patent No.: US 6,268,128 B1
(45) Date of Patent: *Jul. 31, 2001

(54) IMMOBILIZED OLIGONUCLEOTIDE PROBES AND USES THEREOF

(75) Inventors: Mark L. Collins, Holden, MA (US); David V. Morrissey, Middletown, CT (US)

(73) Assignee: Vysis, Inc., Downers Grove, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 07/902,517

(22) Filed: Jun. 22, 1992

Related U.S. Application Data (63) Continuation of application No. 07/321,728, filed on Mar. 10, 1989.

(51) Int. Cl.[7] .............................. C12Q 1/68; C12M 1/40; C07H 21/04; C07H 21/02

(52) U.S. Cl. .......................... 435/6; 435/259; 435/287.2; 435/288.3; 435/288.4; 435/288.7; 436/501; 436/508; 536/23.1; 536/24.2; 536/24.3; 536/24.32

(58) Field of Search .................................. 435/6, 7, 810, 435/259, 287.2, 288.3, 288.4, 288.7; 436/501, 508; 935/77, 78; 536/23.1, 24.2, 24.3, 24.32

(56) References Cited

U.S. PATENT DOCUMENTS

| | | | |
|---|---|---|---|
| 4,358,535 | * 11/1982 | Falkow et al. | 435/5 |
| 4,751,177 | 6/1988 | Stabinsky | 435/6 |
| 4,797,355 | 1/1989 | Stabinsky | 435/6 |
| 5,288,609 | 2/1994 | Engelhardt et al. | 435/6 |
| 5,457,025 | * 10/1995 | Collins et al. | 435/6 |

FOREIGN PATENT DOCUMENTS

| | | |
|---|---|---|
| 0 139 489 | 6/1985 | (EP) . |
| 0200057 | * 5/1986 | (EP) . |
| 0198413 | 10/1986 | (EP) . |
| 0232967 | 8/1987 | (EP) . |
| 0265244 | 4/1988 | (EP) . |
| 0305145 | 3/1989 | (EP) . |
| 2169403A | 7/1986 | (GB) . |
| WO87/03911 | 7/1987 | (WO) . |

OTHER PUBLICATIONS

Wood et al., PNAS (USA), vol. 82, pp. 1585–1588, (1985), "Base Composition—independent hybridization . . . ".*

* cited by examiner

*Primary Examiner*—Stephanie Zitomer
(74) *Attorney, Agent, or Firm*—Kevin M. Farrell

(57) ABSTRACT

The invention is a method of detecting nucleic acids in a sample using oligonucleotide probes which are noncovalently bound to solid supports for rapid, sensitive, hybridization assays. The method involves coating the support surface with a polynucleotide and then hybridizing a specific capture probe for each analyte to the polynucleotide by way of a short tail of the complementary polynucleotide. The immobilized probes are used to capture nucleic acid targets out of complex specimens for nonisotopic detection without the need for prior cell culture or purification of the target nucleic acids. A panel of tests can be run on each specimen simultaneously, a format that conserves precious samples. The assay can be readily automated, and can be conveniently run in a manual fashion on large numbers of samples in two to three hours.

33 Claims, 3 Drawing Sheets

SEQUENCES OF OLIGONUCLEOTIDE PROBES

| PROBE | SEQUENCE (5' → 3') |
|---|---|
| 576 | XXX XXX XXX XXX XXX XXX XXX XXX XXX XXX |
| 676 | TCA ATT GCT GCG GTT ATT AAC CAC ACC TTC CT |
| 732 | TCC AAC TGT TGT CCT CTT GTG TAG GGC AGA TTA AC |
| 888 | AAA AAA AAA AAA TGT GTT AAG CAG GAG TAT AGA GTA TTA GCA GTC GT |

X = ANY OF THE FOUR NUCLEOTIDES

*FIG. 3*

IMMOBILIZED OLIGONUCLEOTIDE PROBES AND USES THEREOF

This is a continuation of co-pending application Ser. No. 07/321,728 filed on Mar. 10, 1989.

BACKGROUND

Biological samples generally contain nucleic acid sequences which encode information unique to its biological source. For example, all species of acteria which belong to a certain genus (e.g., Campylobacter or Enterobacter) share certain physical characteristics which are encoded by the same nucleotide sequences present in most or all of the species within the genus. Thus, an assay which is specific for the genus can be based upon these common nucleotide sequences.

Detection of nucleotide sequences in a sample can be carried out using nucleotide probes specific for these target sequences. For example, Nagata et al., *FEBS*, 183:379–382 (1985), describe the use of UV irradiation to bind heterologous high molecular weight DNA to polystyrene microtiter wells in order to detect specific sequences within the immobilized DNA by way of specific DNA probes.

Zouali and Stollar, *J. Immuno. Methods*, 90:105–110 (1986), describe a technique for the attachment of high molecular weight nucleic acids to polystyrene microtiter wells using pre-treatment of the support with UV irradiation.

Polsky-Cynkin et al., *Clinical Chemistry*, 31:1438–1443 (1985), describe the use of immobilized capture probes in clinical assays.

Kremsky et al., *Nucleic Acids Research*, 15:2891–2909 (1987) and Wolf et al., *Nucleic Acids Research*, 15:2911–2926 (1987) describe a technique for the covalent attachment of oligonucleotides to latex coated polystyrene beads.

Stabinsky, U.S. Pat. No. 4,751,177, describes a single-step target capture that utilizes a hybridization of a tailed capture probe in solution followed by a solid phase capture with oligo-(dT)-controlled pore glass.

Soderlund, UK Patent Application GB 2169403A (1985), describes several affinity-based capture hybridization methods which use two probes, detector probe and a capture probe that contains one member of an affinity pair.

Collins, European Patent Application Number 265 244, describes a nonisotopic reversible target capture protocol which makes use of dA-tailed oligonucleotide probes and oligo(dT)-magnetic particles and poly(dT) filters.

Presently available nonisotopic assay methods are either lacking in sensitivity for certain applications, or are too complex or too slow to be clinically useful. They also require a sample to be split in order to perform multiple assays thereon, resulting in decreased sensitivity. Most of the prior art methods also employ solid phases that are not easily separated from viscous clinical samples, such as stool. It would be helpful to have a rapid, nonisotopic assay useful for assaying complex or unpurified samples that is highly specific, simple to use useful with RNA as well as DNA targets and applicable to clinical and food samples with no prior purification of the nucleic acids of the samples.

SUMMARY OF THE INVENTION

The present invention pertains to a method of determining (detecting and/or quantitating) target nucleic acid sequences in a sample, which is simple and rapid and does not require the use of radioactive materials. In the method of the present invention, oligonucleotide probes (capture probes), which are specific for nucleic acids to be detected (target nucleic acids), and bound to an appropriate support, are contacted with a sample to be analyzed for the target nucleic acids, under conditions appropriate for hybridization of complementary nucleic acid sequences to occur. In general, the sample has been previously treated in such a manner that the molecular structure of the cells is disrupted (i.e., the cell structure, such as the chromosomes and membranes are broken, and the cellular cytoplasm is dispersed).

In the method of the present invention, a sample is treated to release the nucleic acids of cells contained in the sample, and is combined with a capture probe, which is reversibly attached or preimmobilized on a support, such as polystyrene, by means of a homopolymer tail whose sequence is complementary to a sequence present on the support surface. Hybridization of complementary nucleic acid sequences results in capture of target nucleic acids from the sample. Capture of the target on the solid supports also serves to separate the target nucleic acids from sample impurities prior to nonradioisotopic or radioisotopic detection. Target nucleic acids can be detected and/or quantified by hybridizing the captured target with a labeled probe, for example.

The present method has numerous advantages over presently-available methods. For example, the present method makes it possible to: (1) analyze many samples (e.g., 20 or more) nonisotopically in a short time; (2) carry out analyses without sample filtration or cell culture or prior purification of nucleic acids; (3) run a panel of tests on a sample simultaneously without crosstalk; (4) run multiple tests on a small volume sample; and (5) use capture probes without prior purification. In addition, the method can be efficiently performed using a single labeled probe, since one generic probe can be constructed (e.g., by cloning) to hybridize to all target nucleic acids that make up a screen or a panel. The present assay method allows the non-radioactive detection of as little as one hundred attomoles of target nucleic acid in any type of cell extract (bacterial, mammalian, yeast, plant), in food and clinical samples and other impure biological specimens in about two hours.

In addition to its use in detecting and/or quantitating the level of target present in a sample, the present invention can also be used, without the customary phenol extraction, to isolate nucleic acid targets from crude specimens for cloning (or subcloning) and/or amplification. Substantial purification of the target prior to either cloning or target amplification (such as the PCR method, Mullis, U.S. Pat. No. 4,683,202) reduces the level of background (and thus improves the specificity) of these procedures as well as removing numerous interfering substances present in crude specimens. In addition, if necessary, the sensitivity of the detection of targets by the present method can be substantially improved by inserting an optional target amplification method between target capture and detection or by using reversible target capture methods as disclosed herein.

The method of the present invention is particularly useful for precious or small volume samples because it is not necessary to divide the sample into smaller samples for each test to be carried out. Another advantage of the present invention is that a nonspecific or generic reporter probe can be used because the possible loss of signal due to the presence of interfering substances or high levels of competitor organisms is avoided by capturing target nucleic acid sequences from the sample being tested prior to labeling.

The present invention also includes kits for rapid analysis of samples by the method of the present invention. A kit can contain, for example, suitable solid supports, such as dipsticks or wells, which contain a substratum, which is discussed in greater detail hereinbelow, and a specific capture probe prehybridized to the substratum, and an agent, such as a lysis solution, for disrupting cells to free cellular nucleic acids for detection. Alternatively, the kit can contain capture probes which are not bound to the solid phase. This requires the user to perform the prehybridization step. Such a system allows the user more flexibility since the user would prepare the appropriate capture probe-solid phase adducts whenever desired. The kit can, optionally, contain a labeled probe and a means for detecting the labeled probes, positive and/or negative control samples, elution buffers for carrying out reversible target capture and amplification or cloning reagents.

DETAILED DESCRIPTION OF THE INVENTION

The present invention relates to a rapid, nonisotopic method of determining (detecting and/or quantitating) nucleic acid sequences of interest (target nucleic acid sequences) in a sample, as well as a method of isolating or purifying target nucleic acid sequences (e.g., for the purpose of amplification or cloning), materials useful in carrying out the method and kits containing such materials, useful for determining target nucleic acid sequences in a sample.

In the method of the present invention, a complex sample to be analyzed for the presence of one or more of the target nucleic acid sequences is combined with a solid support which has affixed to or immobilized on its surface nucleic acid sequences, or probes, referred to as "capture nucleic acid sequences" or "capture probes". The capture probes are complementary to the target nucleic acid sequences, and, under appropriate conditions, will hybridize with the target nucleic acid sequences.

The capture probes are bound to a poly-nucleotide layer or substratum, which is discussed in greater detail below, which is coated directly onto the solid support, through a "tail" which is complementary to the substratum.

The present method can be used on any sample which contains nucleic acids. The sample must be sufficiently liquid to allow contact with the probe and for hybridization to occur. The sample can be complex, clinical samples, such as, mucus, sputum, urine, stool, or blood, or foods or beverage, such as milk, cheese, wine or prepared foods. The sample does not have to be separated, filtered or precultured prior to use of the present method. The sample is generally pretreated with an agent which disrupts molecular structures within the cells.

These agents are referred to as "agents that disrupt molecular structures" (e.g., "chaotropic agents"), and will disrupt the cells, or viruses, present in the sample to release nucleic acids. Such agents are generally compounds or solvents which disrupt the molecular structure of a cell, that is, these agents are capable of denaturing the secondary, tertiary and/or quarternary structures of biopolymers, including proteins, nucleic acids and polysaccharides, that are generally found in specimens. Examples of agents that disrupt molecular structures are chaotropic salts (e.g., guanidinium thiocyanate), and monovalent salts of large acidic anions (e.g. trichloroacetate, trifluroacetate), denaturing detergents (e.g., dodecyl sulfate), hydrolytic enzymes (e.g., proteases), and compounds which disrupt hydrophobic bonds (e.g., phenols, dimethyl formamide, dimethylsulfoxide, tetramethyl urea, guanidinium hydrochloride) or hydrogen bonds (e.g., urea, formamide). Physical or mechanical means of disrupting molecular structures, e.g., sonication, can also be used to release nucleic acids. Agents that disrupt molecular structures can be used singly or in various combinations to achieve a desired result.

Solid supports which can be used in the present invention include any solid material to which can be bound sufficient amounts of the substratum poly-nucleotide to allow the capture probe to be pre-hybridized to the support. Polymeric materials, such as agarose beads or polystyrene, are generally useful as supports.

Polystyrene is a particularly useful support for use in the present invention because it can bind large amounts of polynucleotide substratum material, allows facile nonisotopic detection of targets, and has relatively low nonspecific binding of both enzymes and nucleic acids. By "nonspecific binding" is meant the target-independent binding of a probe to a solid support. The forces responsible for the sticking are not well understood (hence the use of the word 'nonspecific'), but van der Waals bonds, hydrophobic bonds, and hydrogen bonds are thought to be likely contributors to the total energy of the binding. The labeled probe may be uncomplexed but more likely is complexed with one or more cellular components that enhance the tendency of the probe to bind to the solid support. It is measured by incubating the sample or specimen, the labeled probe, the capture probe, and solid support in the absence of the target, and in the absence of any "pseudo targets" (i.e., targets closely resembling the actual target) with which nonspecific hybrids may form. The configuration of the support will vary depending upon the type of assay and the nature of the samples to be assayed. Configurations such as microtiter wells, tubes and dipsticks are useful in the present invention and allow the simultaneous assay of a large number of samples to be performed manually in an efficient and convenient way. The assay can also be automated using, for example, microtiter wells and is capable of extensive automation because of automatic pipetters and plate readers. Other solid phases, particularly other plastic solid supports, may also meet these basic criteria (including the ability to adsorb large amounts of polynucleotide) and thus be suitable for use in the present invention.

A substratum or layer is coated onto the supports. The 'substratum' is a layer of material that is laid down on a solid support by covalent or noncovalent means, which greatly enhances the binding of the next layer of material. The substratum can be any polynucleotide. The polynucleotides can be from about 50 to about 3000, or more, nucleotides in length. About 1500 to 3000 nucleotide bases is a particularly useful length. Preferred substrata materials are homopolynucleotides such as homopolymers of deoxyribothymidylate (dT), deoxyriboadenylate (dA), deoxyribocyfidylate (dC) or deoxyriboguanylate (dG). Poly(dT) and poly(dA) are particularly preferred substrata for the present invention. However, mixed sequences comprising simple repeating polynucleotide sequences, having repeat sequences no longer than about a tetranucleotide, can be used. For example, alterating nucleotides (e.g., GTGT or GGTTGGTT) can be used as the substratum, wherein the length of each repeat sequence is four nucleotides or less. In general, about 250 ng to about 1 µg of substratum is bound to the support.

Binding a substratum or layer of material to a solid support (such as polystyrene) allows the binding of a multiplicity of oligonucleotide capture probes (up to about 1 µg), which in the absence of the substratum do not bind to the solid support (<1 ng to polystyrene). More than one substratum layer can be bound to a support. For example, large adaptor molecules containing short tails, as well as a multiplicity of properly spaced secondary ligands, can be bound to a poly(dT) (or other polynucleotide) substratum bound to polystyrene. The multiplicity of secondary ligands constitute the second layer or second substratum. Thus many first probes or other adaptor molecules can bind to the solid support and each of them would be capable of binding a plurality of capture probes. Additional layers can be added as needed. In this way the capacity of the solid support can be increased to any desired level to improve the speed and efficiency of the capture of target molecules.

The capture probes are mixed base nucleic acid sequences, which are specific for the target nucleic acids to be detected. The mixed base sequences of the probe allows it to base-pair only with the complementary sequence of the target nucleic acid, under appropriate conditions of stringency. That is, the capture probe may bind "pseudo targets" which have sequences which are closely, but not exactly complementary to the mixed base sequence of the probe, forming nonspecific hybrids. Nonspecific hybridization can be reduced under stringency conditions. (Stringency is described below, and in detail in Example 6). The specific sequence of the capture probe will depend upon, and be complementary to, the nucleic acid sequence of the target nucleic acid. The probe can be DNA or RNA.

The capture probes are bound, via a "tail", to the substratum present on a solid support. The tail is an RNA or DNA sequence that is complementary to the substratum. The tail can be added either synthetically or enzymatically to either the 5' or 3' end, or middle, of the capture probe. Thus, if the substratum is poly(dT), a complementary tail would consist of poly(dA). Oligonucleotides (i.e., about 10–50 nucleotides) are preferred as capture probes over polynucleotides (i.e., more than about 50 nucleotides) because of the former's greater specificity. Oligonucleotides can readily distinguish a perfectly formed double helix (exact match) from just a single-base pair mismatch. This exceptional specificity has been termed "allele specificity". Connor, B. J. et al. (1983), *Proc. Natl. Acad. Sci. USA*, 80, 278–282 describe the allele-specificity of oligonucleotides generally. Collins and Hunsaker, (1985), *Anal. Biochem.*, 151, 211–224 describe the allele-specificity of tailed oligonucleotides.

The tailed capture probe is reversibly or noncovalently bound to the substratum. That is, the binding of the tail to the substratum can be changed by a simple physical stress, such as increasing the temperature or the chaotrope concentration. Thus, capture probes bound to a poly(dT) substratum via a (dA) tail can be readily removed, after binding with the target nucleic acid for further processing.

This can be done for example, simply by adding heated buffer to the polystyrene or increasing the concentration of a chaotrope or nucleic acid denaturant above a certain threshold level. The probe-target complex can be recaptured by cooling, or by a simple dilution of the nucleic acid denaturant.

In one embodiment of the present invention, UV or gamma radiation is used to bind the homopolynucleotide substratum, such as poly(dT), to solid supports, such as microtiter wells, dipsticks, and tubes. The process of binding a polynucleotide substratum to a substrate is described in detail in Example 1.

The tailed capture probe is immobilized on the substratum by prehybridizing the probe with the substratum. That is, the tailed probe is hybridized to the substratum complementary sequence prior to use in an assay. In the preferred method, the substratum sequence is poly(dT) and the tail is poly(dA). However, other simple repeating sequences can be substituted for the dA-dT affinity pair. The repeating sequences should preferably be no longer than about a tetranucleotide (i.e., 4 nucleotide bases) in order to provide the rapid hybridization kinetics that would be desirable in a manufacturing process. In prior art methods, the tailed probe is added by the user to the specimen, and bound to the target in solution and then bound to the solid support. That format is disadvantageous in that multiple tests cannot be performed on each sample, and the tail on the capture probe must be long to overcome steric hindrance in the approach of the target to the support. In the present method, the user simply combines one or more solid supports, already containing bound capture probes, and the sample and maintains the resulting combination under conditions appropriate for hybridization of complementary sequences to occur.

More than one type of immobilized oligonucleotide capture probe can be contacted with a single sample at one time, thus making it possible to analyze the sample for more than one target nucleic acid sequence at a time. For example, different solid supports specific for different bacterial genuses can be used simultaneously to test one sample for the presence of the bacteria. The stability of the linkage between the probes and the substratum substantially prevents cross-hybridization, or "cross-talk", among the different types of probes. The term "crosstalk" means interprobe exchange of capture and or target oligonucleotides. That is, where one or more dipstick probes is contacted with a sample, a capture oligonucleotide bound to one of the dipsticks, which may or may not be hybridized with a target nucleic acid, detaches from the dipstick and becomes bound to another dipstick in the sample. This migration of probes between dipsticks is "crosstalk". The term can apply to other support configurations besides dipsticks, which was used merely to illustrate the present example.

Prehybridizing the capture probe to the support eliminates the need to purify the capture probes after the tailing reaction. Only oligonucleotides with a tail of sufficient length will bind to the coated polystyrene.

Prehybridization also helps to overcome potential interference from endogenous poly(A) or poly(dA), which interference is potentially significant in clinical samples containing a large number of human cells. Capture probes with very short tails can be used since the target cannot sterically hinder the tail's attempt to bind to the solid support. The tail length need only be sufficiently long to form stable hybrids with poly(dT) in the buffer employed. Reduced tail length also decreases the cost of the capture probes. The preferred tail length is from about 15 to about 30 nucleotides.

In the method of the present invention, oligonucleotide capture probes preimmobilized on solid supports by way of the homonucleotide affinity pair are contacted with the sample for direct detection of specific microorganisms in the samples. For example, Campylobacter has been detected directly in clinical stool samples with about 90% specificity and sensitivity. The assay can detect Campylobacter and Salmonella seeded in 25% w/v normal stool at less than $1.0 \times 10^5$ cells/ml.

The method described herein simplifies sample handling and processing in that filtration normally required for stool and other viscous or chunky samples is omitted and pipetting can be minimized due to the ability to add one dipstick for each test to every sample. The preimmobilization of the capture probe on a solid support allows simultaneous analysis of each and every clinical sample for a number of different analytes.

In the present method, specimens are first dissolved by a chaotropic agent (e.g., a solvent disrupting molecular structures). By doing capture in a chaotropic solvent which disrupts the molecular structures of the target cells or viruses prior to labeling, other substances that could potentially interfere with this nonisotopic assay, such as endogenous biotin, avidin, avidin-like molecules, nucleases, proteases, and nucleic acid binding proteins, are removed prior to the introduction of the labeled generic probe. A number of immobilized capture probes, for example, polystyrene dipsticks, each with a different specific capture probe (including an optional nonsense control sequence), is then placed into each sample to remove target molecules complementary to each of the probes. The dipsticks are removed from the specimens, washed, labeled, for example, with a generic reporter probe, and detected nonisotopically. Nonisotopic detection can be carried out using the biotin-streptavidin-alkaline phosphatase system described by Leary et al. in *Proc. Nat'l. Acad. Sci. USA*, 80:4045–4049 (1983). The targets can also be labeled with labels such as fluorophores, chemiluminescent compounds or radioisotopes and detected using standard methods.

The present method optionally includes a "stringency" wash step. A stringency wash is a wash protocol that reduces nonspecific hybridization. A nonspecific hybrid is an imperfect hybrid, that is, one that contains mostly correct base pairs, but has one or more mismatched bases (e.g., A not paired with T or U; C not paired with G). Nonspecific hybrids generally have a lower dissociation temperature than the perfectly base-paired hybrid between the actual target and the capture probe. Nonspecific hybridization results in a complex of a capture probe and a "pseudo-target", which is a molecule that closely resembles the actual or real target in its base sequence. The temperature of a stringency wash is generally about 1–5° C. below the dissociation temperature of the capture probe-target complex, but just above the dissociation temperature of any capture probe-pseudo target complexes that may be present. A quaternary salt, such as tetraethyl ammonium chloride (TEA Cl) can be used for the stringency wash. For example, at a concentration of 2.4M, TEA Cl confers equivalence to G-C and A-T base pairing, allowing the stringency of hybridization to be controlled at a single temperature (for a fixed probe length) in a manner that is completely independent of GC content. Wood, W.I., et al., (1985), *Proc. Natl. Acad. Sci*, 82:1585–1588. Since TEA Cl strengthens A-T base pairing in relation to G-C, it was employed as a wash reagent to maintain tight binding of the dA-tailed probe to the poly (dT) coated support while decreasing the strength of mismatched hybridization reactions between the mixed base sequence oligonucleotide capture probe and any nucleic acid sequences closely resembling the true target. Two surprising aspects of the TEA Cl wash in the present system are that (1) non-specific binding of the labeled probe to the solid support is decreased while, (2) hybridization signals are increased when the wash is applied prior to the addition of labeled probe.

It has now been shown that the level of subsequent binding of the labeled probe to captured targets is increased by up to a factor of eight when the TEA Cl wash step is applied prior to the addition of the labeled probe. Washing with TEA Cl prior to the addition of labeled probe causes a decrease in the level of the nonspecific binding of the labeled probe to the support during the subsequent labeling reaction. Similiar results have been demonstrated with 2.4M TEA Br and can be predicted with the use of related salts/solvents.

Without wishing to be bound by theory, it is believed that the TEA cations remain bound to the poly(dA)-poly(dT) for a significant period of time and somehow alter the structure of the immobilized probe-target complex with the result that the target becomes more accessible to incoming riboprobes, thus increasing the hybridization efficiency. For example, the target rRNA may have its elaborate secondary structure relaxed in TEA Cl. Orosz and Wetmur, (1977), *Biopolymers*, 16:1183–1199 describe the relative instability of the RNA-RNA double helix in TEA Cl. For a short period of time the target may be more accessible to the incoming riboprobe, causing an overall increase in the level of hybridization.

In addition to the format described above, the present method can be used in a "reversible target capture" format. By "reversible target capture" is meant the following process: A target is immobilized on a first solid phase. The first solid phase is washed and the target is removed by addition of the first elution buffer and immobilized on a second solid phase. The second solid phase is washed, and, optionally, the target is removed with a second elution buffer and immobilized on a third solid phase. The process can be repeated as often as desired. The process of reversible target capture greatly enhances the signal/noise ratio of the hybridization assay. The solid phases can be the same or different; the elution buffers can be the same or different. Generally, maximum signal/noise ratios are achieved when both the solid phases and the elution buffers are different.

Formats for reversible capture include, for example:
1. Targets are captured with short-tailed (e.g., having a dA tail about 15 nucleotides long) oligomer probes (about 35–50 nucleotides in length) which are prebound to polystyrene, in a tetraalkylammonium salt. If desired, a specific labeled probe can be added during the first capture. If a generic labeled probe is desired, it can be added to the elution buffer. Elution is performed using 2.5 M GuSCN and recapture is done with a second oligonucleotide containing a longer tail (e.g. a dA-50 or dA-100 tail) which will form stable hybrids with poly(dT) in 2.5 M GuSCN. (2 oligoprobe specificity, 3 if a specific labeled probe was used).
2. Targets are captured with short-tailed (e.g., about 15 nucleotides) oligomer probes (e.g., about 35–50 nucleotides in length) prebound to polystyrene in a tetraalkylammonium salt. If desired, a specific labeled probe can be added during the first capture. If a generic labeled probe is desired, it can be added to the elution buffer. Elution is performed with 2.5M GuSCN. GuSCN is then diluted so that the short tailed probe can rebind to poly (dT). (1 oligo probe specificity or 2 if a specific labeled probe was used).
3. Targets are captured with a short oligomer (e.g. about 15–20 nucleotides) and a long tail (e.g., dA-100 or more). A specific labeled probe can be used during the first capture; a generic labeled probe is best used during the elution. The target is then released by contacting with a tetraalykylammonium salt that stabilizes poly(dA)--poly(dT) relative to mixed base sequences. The tailed probe remains bound to the support; the target is released. The target is then recaptured with a second specific oligomer to improve the specificity of the hybridization and reduce the nonspecific binding of excess labeled probe to the solid supports. (2 oligo probe specificity, 3 if a specific labeled probe was used).

4. In the preferred method, the first capture probe is prebound to the first solid support. A second mixed base sequence can be prebound to the second solid support. The next step is to capture the target on the first solid support. A specific labeled probe is best added during the first capture while a generic labeled probe is best added to the elution buffer. Elution is done in such a way as to remove only the target, or the target and the first capture probe. It is preferable to add a specific labeled probe to the elution buffer if the process of elution would dissociate a previously added labeled probe from the target. The sample is either cooled or diluted, as required, and added to the second solid support. The poly(dT) of the second solid support was pre-saturated with the second capture probe well enough to prevent any significant rebinding of the target to the second solid support through the tail of the first capture probe. In other words, the target is forced to rebind to the support by hybridization to the second specific mixed base sequence (2 oligo probe specificity,or 3 oligoprobe specificity if a specific oligomer labeled probe was used)

By adding an appropriate amount of poly(dT) to the elution buffer, the poly(dA) of the first capture probe can be prebound to the poly(dT) in solution before it has a chance to bind to the second support. This method has been employed successfully to block poly(dA)-containing molecules from binding to poly(dT) supports containing prebound tailed probes in a co-pending application entitled "Methods and Apparatus Useful in Preventing Endogenous Substances from Interfering with Affinity Capture Schemes" by Collins, Gillespie and Morrissey, Attorney's docket number ITG88-02, filed concurrently herewith.

Poly(dA) can be incubated with the second solid phase prior to the addition of the sample that eluted from the first solid phase with the first tailed probe. This will effectively preblock any free poly(dT) on the second solid phase so that no poly(dA) from the first tailed probes can bind to the second solid support.

It should be noted that the procedures described above are not limited to just two captures, but can be extended to any desired number of captures. However, if more than two are employed, the assay is more suitable to automation than for manual use. In addition, the second or even the third solid phases (with triple capture) do not have to be of the same chemical composition as the first. Indeed, advantages have been disclosed for the use of very different solid phases in reversible target capture (Collins, European Patent Application Number 87309308.2).

The assay steps of the present method can be readily automated. This is especially so with microtiter plates as the solid phase, since automatic pipeting equipment (for reagent addition and washing steps) and color readers already exist for microtiter plates. An automated device for carrying out the present invention can comprise: a pipetting station and a detection apparatus, said pipetting station being capable of performing sequential operations of adding and removing reagents to the solid phase at specific time points in a thermostatted environment (i.e., temperature controlled environment). The sequential operations include one or more of the following: mixing or contacting samples, lysis solutions and solid support, withdrawing fluid from the supports, adding wash buffer, repeating the steps enumerated above, adding labeled probes, repeating the wash steps again, adding detection agents, and detecting the signal with the detection apparatus.

The present preimmobilized oligonucleotide probes and method of using them can be incorporated into a kit for clinical use. Such a kit would include solid supports each having bound thereto a substratum, and one or more specific tailed capture probes prehybridized to the substratum. The substratum will preferably be a homopolynucleotide, such as poly(dT). The kit can also contain lysis solutions or other chaotropic agents, and a labeled probe for detecting and quantifying target nucleic acids. The kit can optionally contain wash buffers, a means for detecting the labeled probe, one or more elution buffers, amplification or cloning reagents, and/or one or more positive control samples and one or more negative control samples. Amplification of the target sequences can be accomplished, for example, by the technique described by Mullis in U.S. Pat. No. 4,683,202. Cloning of the target sequences can be accomplished, for example, by the method disclosed by Maniatis in *Molecular Cloning: A Laboratory Manual*, Cold Spring Harbor Laboratory, Cold Spring Harbor, N.Y. (1982).

The invention will now be further illustrated by the following examples, which are not intended to be limiting in any way.

EXAMPLES

Example 1

This example shows that laying down a poly(dT) substratum on polystyrene greatly increases the ability to bind the preferred oligonucleotide capture probes to this solid phase, which in turn improves the ability to do target capture on this support. It further discloses methods for preparing multilayered substrata to increase the binding capacity of the support for the capture probes, and thus, to increase the speed and efficiency of target capture.

Materials and Methods

Coating of Polystyrene with Poly(dT)

The following procedure is for coating microtiter wells, but has also been used successfully for coating polystyrene tubes and dipsticks such as those produced by Hygeia, Inc. (Newton, Mass.). Removawell strips were used to customize the number of wells to be used per test. A volume of 0.3 ml of 3 OD/ml poly(dT) in 1.5M NaCl, 0.3M Trips (pH8.0), 0.5M $MgCl_2$ per microtiter well (such as Dynatech Immulon 2) was sealed and incubated overnight at 37° C. The dT mixture was then removed from the wells, which were dried at 37° C. for 30 minutes. The dried wells were exposed to 650 $\mu W/cm^2$ of UV (254 nm) for 2 minutes, washed three times with 1M NaCl, 100 mM Tris (pH9.3), 2 mM $MgCl_2$, 0.1% Tween 20, and air dried. Wells were blocked with 0.5M LiCl, 2.5% acetylated BSA, 10 $\mu g/ml$ denatured *E. coli* DNA, and 10 $\mu g/ml$ tRNA for 1 hour at 65° C., and washed three times as above. Alternatively, 2.5M GuSCN was substituted for 0.5M LiCl and the blocking was done at 37° C. instead of 65° C.

Determination of the Binding Capacity of poly (dT)-Coated Microtiter Wells

To determine the binding capacity of the poly(dT) coated wells, 0.3 ml of $^{32}P$ 5' end-labeled dA12 (5 $\mu g/ml$)

(Pharmacia) in the 1M NaCl wash buffer was added per well and incubated for 15 minutes at room temperature. The wells were washed three times with the above buffer and then scintillation counted. An acceptable dA12 binding capacity for rapid (i.e., 30–60 min) capture was determined by experiment to be greater than or equal to 200 ng/well. Uncoated wells (no substratum) typically had a dA12 binding capacity of less than 1 ng/well.

The binding capacity for oligonucleotides was determined by binding $^{32}$P-labeled tailed oligos to poly(dT)-coated and uncoated (control) wells, which were blocked as described. A binding mixture of 2.5M GuSCN, 2.5% acetylated BSA, 200 mM Tris (pH7.4), 40 mM EDTA, and 2.5 µg/ml of the labeled dA-tailed probe was added to microtiter wells with and without dT3000 coating as a negative control. The mixture was incubated at 37° C. for one hour, removed from the wells (and saved), and the wells were washed three times with the standard wash buffer. Both the wells and the used binding mixture were scintillation counted. To determine the amount of tailed probe bound to the wells, the following formulas were used with C defined as capacity (in micrograms):

$$C = \frac{cpm \text{ added} - cpm \text{ removed}}{Sa \text{ probe } (cpm/\mu g)} = \frac{cpm \text{ bound}}{Sa \ (cpm/\mu g)}$$

From the known specific activity (Sa) of the probe, the amount of tailed probe bound per well was calculated. The results of the two methods showed excellent agreement.

Preparation of Tailed Capture Probes

Oligonucleotide probes were tailed overnight at 37° C. in 0.1M potassium cacodylate (pH7.0), 4 mM $MgCl_2$, 1 mM 2-mercaptoethanol, 0.1 mg/ml acetylated BSA, dATP: oligonucleotide at a 50:1 to 150:1 molar ratio, and 1000 units per ml of TdT (Supertechs). A small amount of tritium labeled dATP was added to the reaction in order to be able to determine tail length and the amount of tailed probe bound per well.

Results

The Salmonella specific 35mer oligo probe #676 (FIG. 3) was 5' end-labeled with $^{32}$P to a specific activity of $10^6$ cpm/µg and tailed with either 30 dA residues or 110 dA residues. The probes were bound to blank microtiter wells and crosslinked with UV as described for the poly(dT) immobilization procedure or they were hybridized to poly (dT)-polystyrene wells in 2.5M GuSCN at 37° C. as described. The wells which were not coated with poly(dT) bound an average (of five wells) of 1 ng of the dA-30 probe and 0.8 ng of the dA-110 probe, a capacity much too low to be useful in a rapid assay format. Surprisingly, an average of 417 ng of the shorter tailed probe and 323 ng of the longer tailed probe were bound to the polystyrene wells coated with the negative control dT3000 substratum, which is significantly higher than what is reported in the prior art with random sequence DNA. Suprisingly, the ability to bind the preferred oligonucleotide capture probe to polystyrene was increased 300–500xfold by using the poly(dT) substratum.

While virtually no dA-tailed oligonucleotide bound to untreated polystyrene using the prior art methods, a substantial amount of the tailed oligonucleotide probe was immobilized on the poly(dT) coated support. Typical levels of bound capture probe range form 250 to 500 ng per well with the entire range producing acceptable results in assays. A larger difference in the amount of probe bound in relation to tail length would be expected. A shorter tail should allow an increased amount of oligonucleotide to bind, although the oligomer with the longer tail is probably not binding to the poly(dT) with all of the nucleotides in its tail.

Increased binding of the tailed probes to the poly(dT)-coated supports has been achieved by increasing the concentration of the oligonucleotide in the binding mixture to 5.0 µg/ml–10.0 µg/ml.

The concept of binding a layer of poly(dT) to polystyrene to allow the binding of a multiplicity of tailed oligonucleotide capture probes, which by themselves do not bind to polystyrene, can be further generalized. For example, tailed probes containing a multiplicity of properly spaced secondary ligands can be bound to poly(dT) polystyrene as above. The multiplicity of secondary ligands constitute the second layer or second substratum. Thus many first probes or other adaptor molecules can bind to the polystyrene and each of them would be capable of binding a plurality of additional capture probes (potentially bound to a target). In this way the capacity of the polystyrene solid support can be increased to any desired level to improve the speed and efficiency of the capture of target molecules.

Example 2

The present invention provides the same assay sensitivity as previous techniques that employ a capture probe free in solution. The rate of capture with the present method is, surprisingly, only slightly slower than the rate with the capture probe free in solution. The rate of capture is thus sufficient for practical clinical use.

Materials and Methods

Coating of polystyrene with polyd(dT) and tailing of capture probes were performed as described in Example 1.

Synthesis of Labeled Generic Riboprobe

A 5' 567bp fragment of the *E. coli* 16S rRNA was cloned into the pGEM4 vector. (Promega Biotec) It was transcribed with T7 polymerase using bio-11-UTP (Enzo) according to the manufacturer's instructions (Promega Biotec). The resulting riboprobe was then purified by two rounds of ethanol precipitation. This probe is capable of hybriding through short stretches of homology to all eubacterial 16S rRNA for which sequence information is available. It has been shown to hybridize to *E. coli*, Shigella, Salmonella, CamEylobacter, Listeria, *Neisseria gonorrhea*, and *Chlamydia trachomatis*.

Binding of dA-tailed Oligonucleotide Probes to Poly(dT) Coated Microtiter Wells Prior to Target Capture A binding mixture of 2.5M GuSCN, 200 mM Tris pH7.4, 40 mM EDTA, 2.5% acetylated BSA, and 2.5 µg/ml of the dA-tailed probe was added to preblocked microtiter wells with and without (negative control) dT3000 coating. The mixture was incubated at 37° C. for one hour, removed from the wells (and saved), and the wells were washed three times with the standard wash buffer. Both selected wells and the used binding mixture were scintillation counted. To determine the amount of tailed probe bound to the wells, the formula set out in Example 1 was used. The two methods used to calculate capacity were in excellent agreement. Control wells which were not coated with polydeoxythymidylate bound an average (of five wells) of 1 ng of tailed probe. Poly(dT) wells typically bind 300–500 ng of tailed probe, depending on the tail length.

Use of Pre-bound Capture Probes in a Nonisotopic Assay

Capture probes can be immobilized either on polystyrene microtiter wells, polystyrene tubes or dipsticks, or other configuration, with all supports functioning equally well for assaying clinical samples. Most of the work has been done with microtiter wells, thus, the following procedure is tailored specifically for this support, though with alterations in volumes, it is easily adapted to dipsticks and tubes.

Three volumes of 1.3×processing buffer (3.25M GuSCN, 0.4M Tris pH7.5, 0.08M EDTA, 13% dextran sulfate, 1% Sarkosyl) were added to clinical samples. After vortexing for 30 seconds at top speed, 300 µl of sample was added to each microtiter well and capture of targets by the pre-bound probe was allowed to occur for 40 minutes at 37° C. (Capture time varies, depending on length of the dA tail on the probe, with approximately one minute allowed for each dA). The samples were then removed from the wells, which were washed with 2.4M tetraethyl ammonium chloride (TEA Cl) for 15 minutes at 37° C. This was followed by the usual high salt wash. A 300 µl volume of a biotinylated generic riboprobe mixture was added per well and incubated for 30 minutes at 37° C. This mixture contained 0.5–1.0 µg/ml of the riboprobe, 2.5M GuSCN, 0.2M Tris pH7.5, 0.01M EDTA, and 10% dextran sulfate. The riboprobe mixture was then removed from the wells, which were washed three times, and the enzyme conjugate (diluted 1:500) was added to the wells (300 µl/well) and incubated for 10 minutes at room temperature. This was followed by three to five washes with the NaCl wash buffer and then the addition of the enzyme substrate pNPP (1 mg/ml) in 1×diethanolamine buffer (Kirkegaard and Perry). The optical density at 405nm was read when the back-ground on the negative control wells started to appear.

Results

Figure 1A:
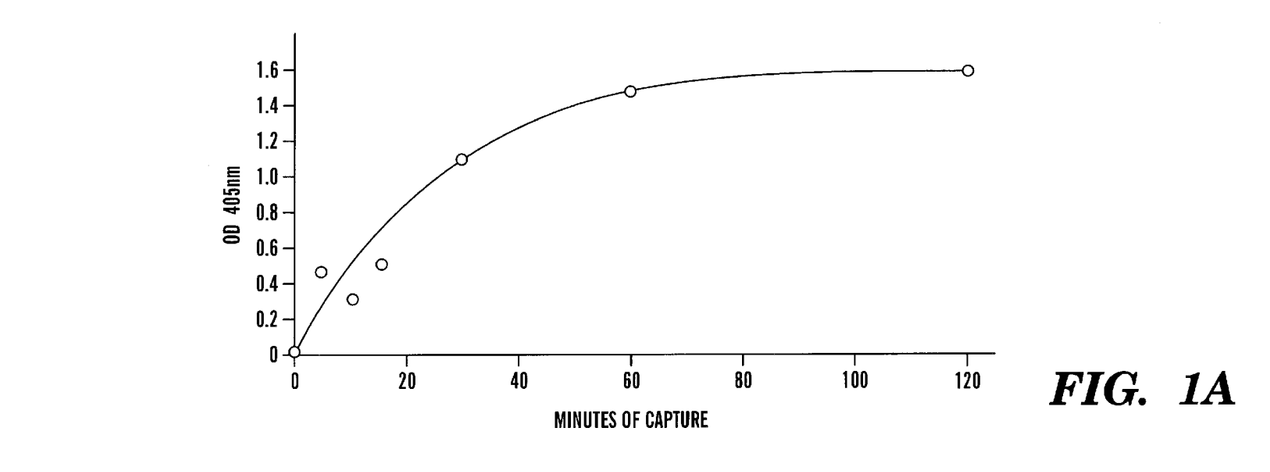
FIG. 1 depicts the rate of capture of rRNA targets with (A) the capture probe free in solution; or (B) with the capture probe prehybridized to the polystyrene.
Figure 1B:
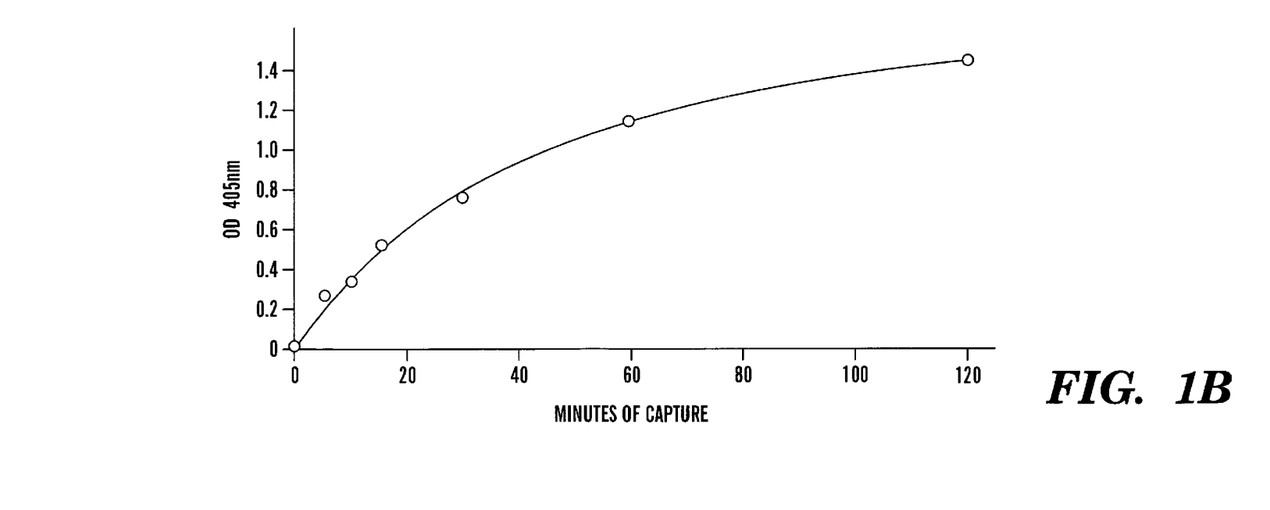

To be a viable rapid assay method for clinical use, the pre-bound probes must function about equally well as capture probes free in solution. That is, the signal/noise ratio must not be significantly worse with the preimmobilized probe and it must not be so slow as to be impractical in a rapid assay format. In order to make this comparison, Campylobacter cell extracts were assayed using a pre-bound capture probe, and also with the hybridization of the capture probe occurring in liquid phase. A Campylobacter specific probe and the target containing 65 dA residues on the 3' end, (hereafter referred to as probe #732 shown in FIG. 3), was bound to poly(dT)-3000 coated microtiter wells as described above. A 300 ul volume of $2.0\times10^6$ Camylobacter cells/ml in $1.0\times10^8$ E. coli/ml in 2.5M GuSCN, 10% dextran sulfate was added to wells with pre-bound 732 probe and incubated for the times indicated in FIG. 1. As a control, samples containing $1\times10^8$ E. coli/ml, but no Campylobacter, were incubated under similar conditions. In parallel, the same samples were preincubated for one half hour with 1 µg/ml of dA-tailed #732 and 1 µg/ml biotinylated generic riboprobe, and added to poly(dT) coated wells for the indicated times. All wells were incubated for the indicated times at 37° C. and then washed three times with 1M NaCl, 0.1M Tris pH 9.3, 2 mM $MgCl_2$, 0.1% Tween 20. The standard assay procedure was then followed as described above for detection. FIG. 1 shows that essentially no difference in the maximum signal was observed between the assay performed with the capture probe either preimmobilized on poly(d)- coated polystyrene or free in solution. Backgrounds were substracted from signals in generating FIG. 1 and were negligible in all cases (less than or equal to 2% of the maximum signal).

A surprising result was that the rate of capture with the dA-65 tailed preimmobilize capture probe was only slightly slower than with the same capture probe free in solution. In FIG. 1, capture is substantially complete in 60 minutes with the capture probe-target complex free in solution and with the dA-65 tailed probe prebound to the support. The capture kinetics with both the free and the preimmobilized tailed probe depends on the tail length. For the preimmobilized tailed probe, the optimal capture time is approximately one minute for each dA residue in the tail; that is, with a tail length of 40, 40 min is allowed for capture; with a tail length of 90, 90 min is allowed for capture. The preferred tail length is about 30–40 nucleotides for quick, efficient capture in 2.5 M GuSCN.

The high concentration of preimmobilized capture probe achieved by the present invention helps to make the hybridization to the target occur quickly. The overall assay times for the two formats are thus about the same (about 2 hours). Table 1 presents a summary of the time required for each step in the method.

TABLE 1

Basic Assay Steps and Times Required Therefor

| Step | Time Required |
| --- | --- |
| Process samples | 2 min/sample |
| Capture with preimmobilized oligos | 40 min |
| TEA Cl stringency wash | 15 min |
| Label with generic riboprobe | 30 min |
| Wash and detect nonisotopically | 30 min |

Note:
20 stool samples have been conveniently assayed in under 3 hours by this method. The capture time is that for a 40 mer dA-tail on the capture probe.

Another factor that is thought to contribute to the unexpected lack of difference in capture kinetics between the free and bound capture probe with a 65mer tail length is that prebound capture probe should still have some mobility in its interaction with the target, since it is anchored to the support only through its tail. If it were nonspecifically immobilized to the solid support through its mixed base sequence (as are probes bound to nitro-cellulose), then it would have less freedom of movement to interact with targets.

Example 3

This example shows that there was no crosstalk among dipsticks containing different prebound probes when these dipsticks were immersed in the same sample. It was shown that the reason for the absence of crosstalk is that the capture probe remains stably bound to the poly(dT) throughout the assay.

When using a number of polystyrene dipsticks in the same sample, each with a different bound capture probe, it is possible that some of the noncovalently bound probe could migrate from one support to another. This phenonemon could result in diminished signals and/or in increased backgrounds. The following experiment was performed in order to see if such "crosstalk" occurs with this method of attaching oligonucleotide probes to polystyrene supports.

A Campylobacter specific dA40-tailed probe (probe #732, FIG. 3) and a nonsense sequence control probe (probe #576, FIG. 3) were bound to poly(dT)-coated polystyrene microtiter wells. These wells were then used in an assay in two different ways: the first being as microtiter wells and the other as "dipsticks" with the entire well being submerged into a sample.

A normal stool sample processed in 2.5M GuSCN, 10% dextran sulfate was assayed with and without the addition of Campylobacter extract at 5.06 cells/ml. Each point was done in triplicate with a total of six "dipstick" wells being added to 10 ml of each stool sample and 300µl of sample being added to each microtiter well. Capture was allowed to occur for forty minutes at 37° C. and was followed by a TEA C1 wash (equal volumes as samples) for fifteen minutes at 37° C. At this point, all of the supports were treated as standard microtiter wells and the protocol described in the Materials and Methods Section was followed. The optical density at 405 nm was read 10 and 30 minutes after the addition of the enzyme substrate. The experiment was repeated using the Salmonella-specific capture probe 676 (FIG. 3) as a control instead of the 576 control probe. In this case, the OD 405 nm was read ten and twenty minutes after the addition of the enzyme substrate. The data of Table 2 shows that neither diminished signals nor any increase in background was observed when "dipsticks" with different bound probes were placed in the same sample.

TABLE 2

Absence of "Crosstalk" Among Dipsticks

| Sample | Support | Probe | OD 405 nm 10 min. | OD 405 nm 30 min. |
|---|---|---|---|---|
| unspiked stool | dipstick | 732 | 0 | 0.044 |
| " | " | 576 | 0 | 0.041 |
| stool + campy | " | 732 | 1.474 | 2.0 |
| " | " | 576 | 0 | 0.030 |
| unspiked stool | well | 732 | 0.004 | 0.064 |
| " | " | 576 | 0.009 | 0.060 |
| stool + campy | " | 732 | 0.529 | 1.226 |
| " | " | 576 | 0 | 0.060 |
|  |  |  |  | 20 min. |
| unspiked stool | dipstick | 732 | 0 | 0.014 |
| " | " | 676 | 0 | 0.006 |
| stool + campy | " | 732 | 1.254 | 2.0 |
| " | " | 676 | 0 | 0.009 |
| unspiked stool | well | 732 | 0 | 0.014 |
| " | " | 676 | 0 | 0.022 |
| stool + campy | " | 732 | 0.584 | 1.133 |
| " | " | 676 | 0 | 0.017 |

Legend: Filtered GTS normal stool #14 in 2.5 M GuSCN, 10% dextran sulfate was spiked with Campylobacter extract at 5.0E6 cells/ml. In the first experiment an average of 556 ng of 732 and 316 ng of 576 were bound per poly(dT) coated well, and in the second, 445 ng of 732 and 350 ng of 676. To each well was added 300 ul of sample and six "dipstick wells" were added to 10 ml of sample. After the TEA Cl wash (in volumes equal to those of the samples), the "dipsticks" were treated as normal microtiter wells and the standard protocol was followed. Results are the average of triplicate samples.

As compared to the results from the wells, the backgrounds from the "dipsticks" were slightly lower (not significantly higher, as predicted if crosstalk occurs) and the positive signals were actually greater (not less, as predicted if crosstalk occurs). The increase in signal seen with the wells used as dipsticks could be due to the larger sample volume available to the wells immersed in the samples coupled with target driven hybridization at this level of target. In any case, the higher signals achieved with the actual immersion of the solid phase as compared to the use of microtiter wells is one advantage of using dipsticks as the solid phase in place of microtiter wells. Another advantage of dipsticks over wells is that sample handling and pipeting are minimized.

Most likely, the absence of crosstalk is due to the tailed probe's remaining bound to the support throughout the capture. Additionally, if a small amount of loosely bound tailed probe does elute from a given dipstick, very little can rebind to other dipsticks since the vast majority of the poly(dT) on the other sticks have been presaturated with their own tailed probes. An experiment was done in order to measure the stability of the prebound tailed probe during the course of the assay. The tritium labeled, dA-tailed capture probe 732 (dA80) was pre-bound in 2.5M GuSCN, 10% dextran sulfate to dT4000 coated and blocked polystyrene microtiter wells with an average dA12 binding capacity of 412 ng. Twelve wells were scintillation counted prior to the assay in order to establish a baseline for the amount of probe immobilized on the supports. The results are presented in Table 3. A mean value of 274 ng of probe bound per well was obtained. Twenty-four wells were then carried through a mock assay which included all of the normal steps and reagents, except that no target or riboprobe were added. Twelve wells were assayed with the standard 2.5M GuSCN, while the other twelve were done with 2.0M GuSCN. 2.0M GuSCN was used because it effectively controls RNase, and oligo(dA) binds to poly(dT) better in 2.0M GuSCN than in 2.5M GuSCN. The wells were incubated with 2.5M or 2.0M GuSCN and 10% dextran sulfate for 40 minutes 37° C., followed by a 2.4M TEA Cl wash for 15 minutes at 37° C. After three washes with 1M NaCl, 0.1M Tris pH9.3, 2 mM MgCl2, 0.1% Tween 20, the wells were incubated once again with GuSCN and 10% dextran sulfate for 30 minutes at 37° C. Following three washes with the above NaCl buffer, the wells were incubated with the enzyme conjugate dilution buffer for 10 minutes at room temperature. The wells were washed three times with the NaCl buffer and then scintillation counted. (The enzyme substrate step was excluded since it may actually be advantageous if the probe came off of the sold support during color development). As seen in Table 3, a mean value of 198 ng of probe retained per well in those which were assayed with 2.5M GuSCN. Based on the pre-assayed values, 72% of the immobilized probe remained bound to the solid supports. For the wells assayed with 2.0M GuSCN, the mean value retained was 218 ng per well, or 79% of the established baseline. This shows that very little capture probe comes off the support during the course of an assay with the present invention.

TABLE 3

Retention of Prehybridized Capture Probe on Poly(dT) - Polystyrene During the Course of an Assay

| Pre-Assay | | 2.5 M GuSCN Assay | | 2.0 M GuSCN Assay | |
|---|---|---|---|---|---|
| opm/well | ng/well | opm/well | ng/well | opm/well | ng/well |
| 15623 | 223 | 12710 | 181 | 12140 | 173 |
| 21056 | 301 | 14001 | 200 | 14563 | 208 |
| 20615 | 294 | 13950 | 199 | 17854 | 255 |
| 22436 | 320 | 16040 | 229 | 17500 | 250 |
| 17037 | 243 | 11269 | 161 | 13340 | 100 |
| 19693 | 281 | 13434 | 192 | 13193 | 188 |
| 18944 | 271 | 14705 | 210 | 16241 | 232 |
| 17898 | 256 | 15822 | 213 | 16020 | 229 |
| 21055 | 301 | 15051 | 215 | 17439 | 249 |
| 20405 | 291 | 13281 | 190 | 17006 | 243 |
| 16609 | 237 | 13947 | 199 | 14330 | 205 |
| 18680 | 267 | 12658 | 181 | 13497 | 193 |

TABLE 3-continued

Retention of Prehybridized Capture Probe on Poly(dT) - Polystyrene During the Course of an Assay

|  | Pre-Assay | | 2.5 M GuSCN Assay | | 2.0 M GuSCN Assay | |
| --- | --- | --- | --- | --- | --- | --- |
|  | opm/well | ng/well | opm/well | ng/well | opm/well | ng/well |
| mean: | 274 | | 198 | | 218 | |
| std. dev.: | 28.3 | | 17.5 | | 27.2 | |
| % retained: | | | | 72% | | 79% |

Legend: Polystyrene microtiter wells were coated with poly(dT)-4000, UV irradiated, and blocked as described. The 3H-labeled, dA-tailed capture probe 732 (dA80) was bound to wells in 2.5 M GuSCN, 10% dextran sulfate. Twelve wells were scintillation counted prior to the start of the assay in order to obtain a baseline of the amount of probe bound. A mock assay (no target or riboprobe added) was done with 24 wells, 12 of which were used with 2.5 M GuSCN and 12 with 2.0 M GuSCN. After the final wash step, the wells were scintillation counted and the percent of the capture probe retained on the wells was calculated.

The retention of the preimmobilized probe is thus about 70–80% during the course of the entire assay. Crosstalk is most likely to occur, if at all, during the first forty minute capture step. During the capture step, retention of bound capture probe is greater than 93%.

It is also possible to add Poly(dT) to the samples to bind to the dA-tails of any probes that elute from their respective dipsticks. This would prevent the dA-tailed probes from binding to a small amount of unhybridized poly(dT) on other dipsticks (by choosing the appropriate concentration of poly(dT), the solution phase hybridization will be faster than the solid phase immobilization).

Poly(dA) could be added to the samples in place of poly(dT) in sufficient quantity such that any free poly(dT) on the dipsticks will preferentially bind the added poly(dA), and not the tailed probes from other dipsticks.

Example 4

This example shows that the present invention can be used to assay clinical stool specimens nonisotopically with no cell culture and without prior purification of the nucleic acids. The sensitivity and specificity are each about 90%.

In two separate experiments, a total of 32 Campylobacter culture-positive stool samples (obtained from Evanston Hospital, Evanston Ill.), and "normal" and culture-negative specimens, were assayed using a pre-bound Campylobacter specific 16S rRNA capture probe (#732). The 732 probe is 35 nucleotides in length and recognizes C. jejuni, C. coli, and C. laridis, but misses all other Campylobacter species, including C. fetus and C. pylori. The standard assay protocol described in the Materials and Methods section of Example 2 was used. The OD 405 nm was read 45 minutes after the addition of the enzyme substrate. For each sample, the level of specific hybridization was computed as the OD 405 nm of the 732 probe well minus that of the control well containing only calf thymus DNA. The cut off for positives was set at twice the average of the negative samples assayed in each experiment. Table 4 shows that of the twenty negative stool samples screened, three were scored as false positive (85% specificity). Better specificity can be achieved by using two specific probes in place of one specific and one generic probe. Significantly, two of the three false positives were from "normal" samples, some of whom may have an asymptomatic low level Camyplobacter infection from prolonged exposure to the pathogen. These samples were not confirmed culture negatives. With confirmed culture negatives, the assay showed one false positive (90% specificity).

TABLE 4

Assay of Normal and Culture Negative Stools with the Campylobacter Probe #732

| Sample | OD 405 nm 732 | CT | 732-CT | +/− |
| --- | --- | --- | --- | --- |

Experiment A: Normal stools from Asymptomatic Gene-Trak Donors

| 1 | 0.106 | 0 | 0.106 | + |
| 2 | 0.006 | 0 | 0.006 | − |
| 3 | 0.122 | 0 | 0.122 | + |
| 4 | 0.035 | 0 | 0.035 | − |
| 5 | 0.030 | 0 | 0.030 | − |
| 6 | 0.072 | 0.028 | 0.044 | − |
| 7 | 0.052 | 0 | 0.052 | − |
| 8 | 0.078 | 0.031 | 0.047 | − |
| 9 | 0 | 0 | 0 | − |
| 10 | 0.028 | 0 | 0.028 | − |

Cut off for positives: 0.094 (2× the avg. of negs.)

Experiment B: Clinical Campylobacter culture-negative stools.

| Z047 | 0.107 | 0 | 0.107 | − |
| Z048 | 0.045 | 0 | 0.045 | − |
| Z055 | 0 | 0 | 0 | − |
| Z061 | 0.071 | 0.001 | 0.070 | − |
| Z065 | 0.124 | 0.015 | 0.109 | − |
| Z070 | 0 | 0 | 0 | − |
| Z080 | 0.219 | 0.441 | 0 | − |
| Z081 | 0.391 | 0.032 | 0.359 | + |
| Z083 | 0.019 | 0 | 0.019 | − |
| Z084 | 0.095 | 0 | 0.095 | − |

Cut off for positives: 0.160 (2× the avg. of negs.)

Legend: See Table 5.

Table 5 shows that twenty-nine of the thirty-two Campylobacter positive clinical samples proved to be positive by the DNA probe assay (91% sensitivity). The three false negatives, which all showed absolutely no signal, may have been missed due to the somewhat limited inclusivity of the capture probe used. It is also possible that the samples were "mishandled" prior to assay since they were not collected and stored with an assay for a fragile molecule like RNA in mind.

TABLE 5

Assay of Campylobacter Clinical Samples

| Sample | OD 405 nm 732 | CT | 732-CT | +/− | Culture |
| --- | --- | --- | --- | --- | --- |

Experiment A: Cut off for positives: 0.094

| Z002 | >2 | 0 | >2 | + |  |
| Z005 | 1.272 | 0 | 1.272 | + | 2P |
| Z006 | >2 | 0 | >2 | + | 3P |
| Z007 | 0.000 | 0 | 0 | − |  |
| Z008 | 0.011 | 0.013 | 0 | − | 2P |
| Z009 | 0.419 | 0.054 | 0.365 | + | 2P |
| Z010 | >2 | 1.343 | >0.6 | + | 1P |
| Z011 | >2 | 0 | >2 | + | 3P |
| Z012 | >2 | 0.786 | >1.2 | + | 3P |
| Z013 | 0.122 | 0 | 0.122 | + | 1P |
| Z014 | >2 | 0 | >2 | + | 3P |
| Z015 | >2 | 0 | >2 | + | 2P |
| Z016 | >2 | 0 | >2 | + | 3P |
| Z017 | >2 | 0 | >2 | + | 3P |
| Z018 | 0.097 | 0 | 0.097 | + | 1P |
| Z019 | >2 | 0 | >2 | + | 3P |
| Z020 | >2 | 0 | >2 | + |  |

TABLE 5-continued

Assay of Campylobacter Clinical Samples

| Sample | 732 | OD 405 nm CT | 732-CT | +/– | Culture |
|---|---|---|---|---|---|
| Z021 | >2 | 0 | >2 | + | 1P |
| Z022 | 0 | 0 | 0 | – | 2P |
| Z023 | >2 | 0 | >2 | + | 2P |
| Z024 | 0.486 | 0 | 0.486 | + | 3P |
| Z025 | >2 | 0 | >2 | + | |
| Z026 | 0.128 | 0 | 0.128 | + | 1P |
| Z027 | 0.416 | 0 | 0.416 | + | 2P |
| Z050 | 1.028 | 0 | 1.028 | + | |
| Z062 | >2 | 0 | >2 | + | |
| Experiment B: Cut off for positives: 0.160 ||||||
| Z064 | >2 | 0 | >2 | + | |
| Z090 | >2 | 0.148 | >1.8 | + | 4P |
| Z091 | >2 | 0 | >2 | + | 4P |
| Z092 | >2 | 0 | >2 | + | 4P |
| Z100 | >2 | 0 | >2 | + | 3P |
| Z112 | >2 | 0.040 | >2 | + | 3P |

Legend of Tables 4 and 5: The "732" column is the Campylobacter specific signal and the "CT" column is the nonspecific (calf thymus DNA) background. +/– refers to whether the sample is positive or negative by the DNA probe assay. Culture: 4P >> 3 >> 2P >> 1P. This represents a relative estimate of the number of Campylobacter colonies on the Campylobacter selective plate.

Example 5

This example shows the detection limit of the assay by measuring the dose-response of the technique for the detection of *Salmonella typhimurium* in 25% w/v normal stool.

Figure 2:
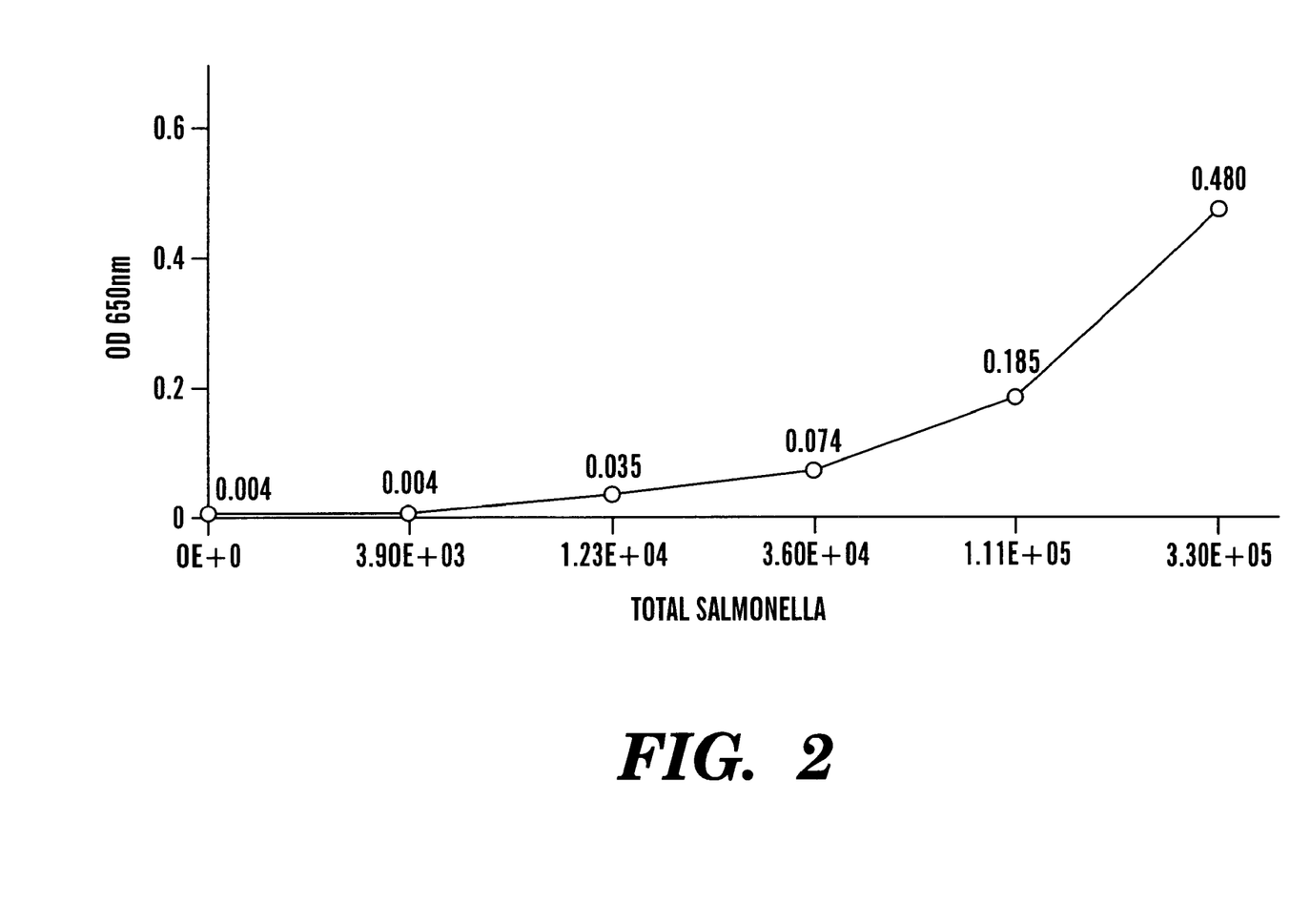
FIG. 2 depicts the dose-response curve for the nonisotopic detection of *Salmonella typhimurium* in 25% w/v normal stool with the present invention.
Figure 3:
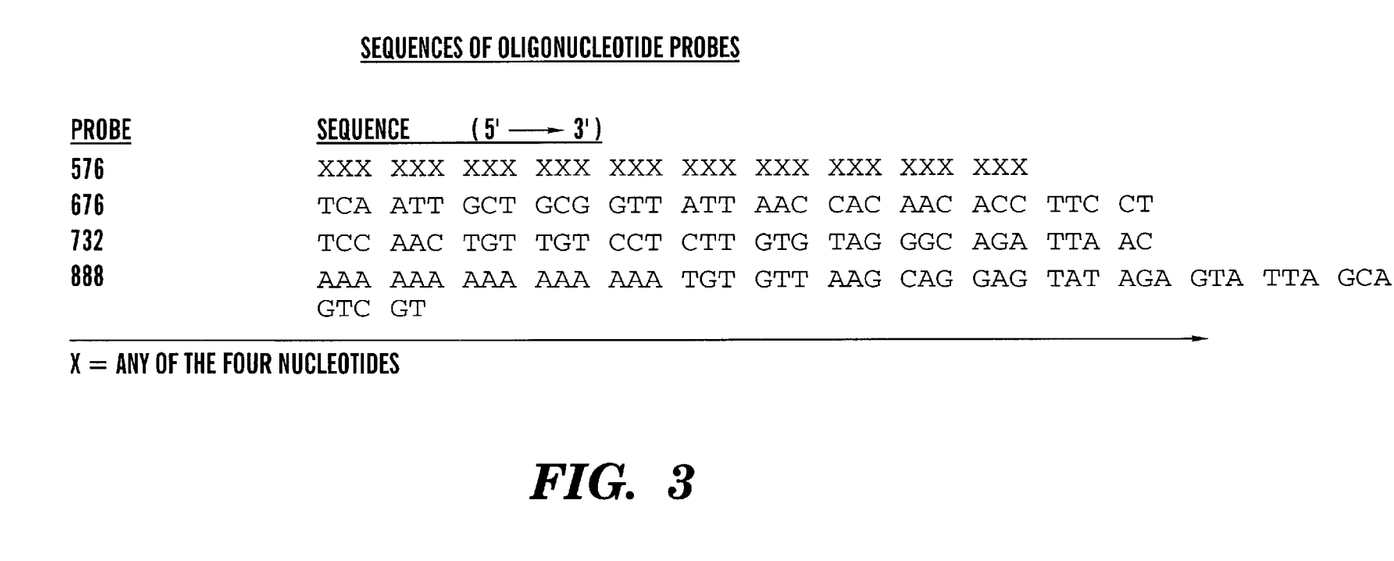
FIG. 3 is a schematic representation of the nucleotide sequence of the oligonucleotide probes used in the present invention.

In order to assess the detection limit of the assay described in this document, a dose-response study was done for the direct detection of Salmonella spiked into normal stool. Normal stool was spiked with various levels of *Salmonella typhimurium* and assayed following the standard protocol of example one but using the Salmonella specific capture probe #676 (FIG. 3). As shown in FIG. 2, the nonisotopic assay detection limit (without cell culture or prior purification of the nucleic acids) is approximately 1.2×104 Salmonella per sample. The signal at that level of Salmonella (0.038 OD) is about 10 times the assay background (0.004 OD).

Example 6

This example shows a useful, generic method whereby a stringency wash can be done with target immobilized on a solid support by means of the poly(dT)-poly(dA) affinity pair.

The wash step with 2.4M TEA Cl following capture of targets out of samples was originally added as a stringency wash in order to reduce nonspecific hybridization. 2.4 M TEA Cl functions as an agent that equalizes the strength of the AT and GC base pairs. This property can be exploited in assays employing a battery of probes of a fixed length but of widely different base composition. By washing with 2.4M TEA Cl, all hybridizations can be made equally stringent. In this way a reduction of nonspecific hybridization can be accomplished with a TEA Cl wash.

Tetraalkylammonium salts have an added advantage for a capture system based on the dA-dT affinity pair: They greatly strengthen the poly(dA)-poly(dT) affinity pair (dissociation temperature of 65° C. in TEA Cl) relative to 35mer mixed base sequences (dissociation temperature of 43–44° C.). This homopolymer thus enjoys an unexpected but useful stability. (Because of the equalizing of G-C and A-T base pairs in 2.4 M TEA Cl, a plot of dissociation temperature versus probe length is a straight line. Wood et al. *Proc. Natl. Acad. Sci. USA.*, vol 82, 1585–1588 (1985). This is true for random mixed base sequences. Poly(dA)-Oligo(dT)-14 and poly(dA)-poly(dT) have dissociation temperatures much higher than predicted by their method.

Because of the special stability of poly(dT)-poly(dA) in reagents such as TEA Cl, a lot of pressure can be applied to dissociate the probe from pseudo-target sequences containing only one or a few mixmatches. The hybridization background can be greatly reduced under such washing conditions. The dA-dT pairing would normally break up under such stress and most of the signal would be lost with the background if it were not for the special and surprising strength imparted to the dA-dT homo-polymer in reagents such as tetraalkylammonium salts.

Example 7

This example shows some further unexpected results obtained with the TEA Cl stringency wash.

Another surprising result was the reduction in nonspecific binding of the labeled probe to the support by washing the support PRIOR TO the addition of the labeled probe (Tables 6, 7, and 8). While the reduction of nonspecific hybridization of the probe to pseudo-targets is expected with TEA Cl, the reasons for the reduction in nonspecific binding to the solid support are not completely understood. While in relatively clean samples the addition of the TEA Cl wash sometimes has little effect on nonspecific backgrounds, it does reduce the higher nonspecific backgrounds encountered in very dirty samples. The lower backgrounds in Table 6 seen with the samples washed with TEA Cl must be due to the decreased nonspecific binding of the labeled probe to the solid support since the control which has no heterologous target is the same as the control that has heterologous target. The lower "*E. coli*" isotopic background seen in Table 8 must also be due to a lower pure nonspecific binding of the riboprobe to the support following a TEA Cl wash (there is far too little homology between the Campylobacter probe and *E. coli* 16S rRNA to form stable hybrids in 2.5M CuSCN at 37° C.).

Another surprising result obtained from the use of reagents such as TEA Cl for washing was the increase in signal when the wash step was done prior to the riboprobe hybridization. Wash steps do not normally increase hybridization signals. This can be seen in the results presented in Table 6, where the inclusion of the TEA Cl wash effectively doubled the signal from the Campylobacter sample (Campylobacter specific capture probe 732 used). The low nonspecific background from the *E. coli* and no cell control samples were further reduced by the TEA Cl wash.

TABLE 6

The Utility of the TEA Cl Wash in a Nonisotopic Assay

| | | OD 405 nm | | |
|---|---|---|---|---|
| Sample | TEA Cl | 732 | 576 | 732-576 |
| Campylobacter | – | 0.744 | 0.016 | 0.728 |
| *E. coli* | – | 0.035 | 0.020 | 0.015 |
| no cells | – | 0.024 | 0.015 | 0.009 |
| Campylobacter | + | 1.487 | 0.021 | 1.466 |

TABLE 6-continued

The Utility of the TEA Cl Wash in a
Nonisotopic Assay

| | | OD 405 nm | | |
|---|---|---|---|---|
| Sample | TEA Cl | 732 | 576 | 732-576 |
| E. coli | + | 0.006 | 0.018 | 0 |
| no cells | + | 0.014 | 0.009 | 0 |

Legend: Campylobacter specific 732 capture probe was pre-bound to poly (dT) polystyrene wells. Cell extracts were diluted in 2.5 M GuSCN, 10% dextran sulfate to 1.0E7 Campylobacter/ml or 1.0E9 E. coli/ml. After the capture step, the wells were emptied and 2.4 M TEA Cl was added to the indicated wells and incubated for 15 minutes at 37 degrees. All wells were then washed 3× in the 1 M NaCl wash buffer and the assay was continued using the standard protocol. The OD 405 nm was read 30 minutes after the addition of the enzyme substrate. The results are the average of duplicate samples.

An experiment was done to determine if TEA Br producted the same effects in the assay as does TEA Cl (Table 8). TEA Br does cause a large increase in signal when used in a wash step prior to riboprobe hybridization. The TEA cation is thus responsible for the effects, although this does not imply that the anion is completely immaterial. Other cations, particularly similar cations, should have the same effect.

TABLE 7

Comparison of TEA Cl and TEA Br Washes

| Sample | Wash | OD 405 nm 20 min. | 60 min. |
|---|---|---|---|
| unspiked stool | — | 0.023 | 0.047 |
| stool + Campy. | — | 0.082 | 0.183 |
| unspiked stool | TEA Cl | 0.030 | 0.065 |
| stool + Campy. | TEA Cl | 0.525 | 1.620 |
| unspiked stool | TEA Br | 0.024 | 0.059 |
| stool + Campy. | TEA Br | 0.488 | 1.504 |

Legend: Normal stool was assayed with and without the addition of Campylobacter extract to 1.0E6 cells/ml. The standard assay protocol was followed with the exception of the TEA Cl wash step, which was varied. In one set of samples it was included, in another it was replaced with TEA Br, and in another it was also excluded. Both the 2.4 M TEA Cl and 2.4 M TEA Br were autoclaved prior to use. The OD 405 nm was read 20 and 60 minutes after the addition of the enzyme substrate. Results are the average of duplicate samples.

Another important aspect of this experiment is that about an eight-fold increase in signal was seen (with both TEA Cl and TEA Br) instead of the two-fold increase previously observed. This could be due to the fact that both reagents were autoclaved before use, which may have eliminated a low level nuclease activity which was previously present (and which thus may have lessened the potential signal enhancement).

In order to determine if the increase in signal seen with the use of reagents such as TEA Cl and TEA Br as wash buffers was due to improved binding of the riboprobe to the target or to a long range effect on alkaline phosphatase activity, an assay was done using a double labeled ($^{32}$P and biotin) riboprobe. Samples were assayed using the Campylobacter specific capture probe 732, with and without the inclusion of the TEA Cl wash following the standard protocol. The OD 405 nm was read 40 minutes after the addition of the enzyme substrate and as expected, the Campylobacter positive signal was approximately doubled with the inclusion of the TEA Cl step (Table 8). Following color development, the wells were washed and then scintillation counted to determine the amount of riboprobe bound to the wells by way of the $^{32}$P label. Approximately twice the number of counts were obtained in the Campylobacter wells which received the TEA Cl wash versus those which did not (The TEA Cl used in this experiment was not autoclaved). This corresponds to the increase in color obtained with the TEA Cl wash step, indicating that this improved signal is due to an increase in riboprobe binding. This increased binding of the riboprobe is believed to represent increased hybridization.

TABLE 8

Effect of TEA Cl Wash on the Subsequent
Binding of the Riboprobe to the Target/
Capture Probe Complex

| Sample | TEA Cl | OD 405 nm | CPM |
|---|---|---|---|
| Campy. | − | 0.596 | 921 |
| Campy. | + | 1.073 | 1753 |
| E. coli | − | 0.089 | 244 |
| E. coli | + | 0.071 | 54 |

Legend: Cell extracts were diluted in 2.5 M GuSCN, 10% dextran sulfate (Campylobacter to 1.0E6 cells/ml and E. coli to 1.0E9 cells/ml) and targets were captured with pre-bound 732 probe for 40 minutes at 37 degrees. The wells were washed with either 1 M NaCl or with 2.4 M TEA Cl for 15 minutes at 37 degrees. The target was then labeled with a + +. + + + + 16S rRNA generic riboprobe which was double labeled with biotin and 32P. After color development with SA-AP/pNPP for 40 minutes, the wells were washed and the amount of 32P bound was determined by scintillation counting.

While a slight decrease in the background from the E. coli sample was observed upon color development when the TEA Cl step was included, a far greater decrease (4.5×) in the amount of riboprobe bound to the wells was seen from the $^{32}$P counts obtained. This 4.5×reduction in background in the $^{32}$P counts represents the true decrease in the level of nonspecific binding of the riboprobe caused by the TEA Cl wash. The failure to see this same level of reduction in color is probably due to variable nonspecific binding of the enzyme conjugate streptavidin-alkaline phosphatase.

The data of Tables 6, 7, and 8 indicate that when the TEA Cl wash step is applied prior to the addition of the labeled probe, the level of subsequent binding (presumably hybridization) of the labeled probe to captured targets is increased by a factor of two or more.

Example 8

This example shows methods whereby the present probes can be used to do reversible target capture. The advantages of a reversible target capture protocol, particularly greatly increased sensitivity and specificity, are fully described in Collins, European Patent Application Number 265244, which has been incorporated herein by reference.

One important advantage of the dA-dT affinity pair used to capture the probe-target complex onto the solid support for the present invention is that it is readily reversible. Reversibility of target capture allows recapture of the target/probe complex onto other solid supports in order to reduce background levels and thus to improve the sensitivity and specificity of the assay. While the preferred user-friendly embodiment of the assay we describe in this document employs only a single capture for ease of use and yet has very good sensitivity and specificity in clinical stool samples, increased sensitivity and specificity may be gained by multiple rounds of capture. The experiment described below demonstrates the feasibility of the first such reversibility scheme. This method would use a capture probe with a very short, chemically synthesized dA tail, in this case dA15. The probe would be immobilized on a poly(dT) coated support in a tetraalkylammonium salt such as but not limited to 3.0M tetramethylammonium thiocyanate (TMA SCN). Tetraalkylammonium salts impart special stability to the poly(dA)-oligo(dT) affinity pair. Following the capture of the target from the sample and subsequent washes, the probe target complex would be eluted from the solid support in 2.5M GuSCN and then recaptured with a second probe with a long dA tail (either with the same or with a different mixed base sequence) on a second poly (dT) support with the same physical composition or with a different composition. As seen in Table 9, high levels of probe 888-dA15 (FIG. 3) bind to poly (dT) coated polystyrene in 3.0M TMS SCN, but not in 2.5M Gu SCN. This shows that targets can be captured in 3.0M TMS SCN; then the probe-target complex can be eluted with 2.5 M Gu SCN to allow subsequent rounds of capture with a second probe containing a longer tail such that the probe-target complex can bind to the poly(dT) in 2.5 M GuSCN. (The concentration of the 888 probe required for acceptable levels of binding to the poly (dT) was increased from the standard concentration of 2.5 μg/ml due to the fact that a crude prep of the oligo was used in the immobilization procedure).

TABLE 9

Binding of dA-Tailed Probe (dA15) to Poly(dT) Coated Polystyrene Wells in Gu SCN and TMA SCN

| Hybrid. Sol. | Probe Conc. | ng bound/well |
|---|---|---|
| 2.5 M Gu SCN | 2.5 ug/ml | 28 |
| 3.0 M TMA SCN | 2.5 ug/ml | 119 |
| 3.0 M TMA SCN | 5.0 ug/ml | 374 |
| 3.0 M TMA SCN | 10.0 ug/ml | 734 |

Legend: 32P labeled 5'dA-tailed 888 (dA15) probe was bound to poly (dT) coated polystyrene microtiter wells in 2.5 M Gu SCN or 3.0 M TMA SCN with 10% dextran sulfate for 1 hour at 37 degrees. Wells were pre-blocked with the standard blocking buffer containing 2.5 M Gu SCN or with substitution by 3.0 M TMA SCN. Following the incubation period with the probe, the wells were washed three times in the standard 1 M NaCl wash buffer and then scintillation counted to determine the amount of probe bound. The data show that this short 5' tailed probe will bind to poly(dT) in 3.0 M TMA SCN but not in 2.5 M Gu SCN. The latter can thus be used as an elution buffer.

Example 9

This example discloses methods employed by the present invention to minimize signal loss due to the presence of large amounts of heterologous rRNAs, endogenous avidin, other biotin-binding molecules and other compounds.

When specimens are being tested for any of a group of pathogens, it is desirable to use a single labeled probe to label all of the targets of interest. For example, for a GI panel, a single large labeled probe (such as the 5' or 3' 16S riboprobe) containing many detectable ligands that would label the 16S rRNA of Campylobacter, Salmonella, and Shigella would be desirable in place of a vast multiplicity of singly or doubly labeled oligomers which would have to be made for each of the organisms (to achieve the same number of reporter groups bound per rRNA target).

However, in a stool sample there are generally more than $10^{11}$ bacteria/ml. Kuritza et al. *Applied and Environmental Microbiology*, 51:385–390 (1986). These bacteria would contain more than $10^{15}$ 16S rRNA per ml, and in a competitive situation, perhaps only $1/1000$ rRNAs of the target organism will be labeled since the labeled probe concentration is only $10^{12}$/ml. This can be corrected by specifically capturing the target out of the stool sample and washing away competitor rRNAs prior to labeling.

Various substances besides rRNAs present inside cells can interfere with the labeling and detection of nucleic acid targets. For example, a biotinylated probe was used in the experiments reported herein. If large quantities of avidin or other biotin-binding macromolecules were present in the sample, these could bind to the biotinylated probe and reduce the size of the signal generated by the streptavidin-alkaline phosphatase. Capture of the target prior to labeling as disclosed herein is a workable solution to this problem.

Another potential interference is endogenous poly(rA) and poly(dA). Mammalian cells, which are found in virtually all clinical samples (especially blood) contain about 1 attomole of poly(rA) per cell. T. Maniatis, et al. 1982. *Molecular Cloning: A Laboratory Manual*, p. 188, Cold Spring Harbor Laboratory, New York. They also contain about 100 ppm poly(dA) by weight. These could compete with the dA-tailed probes potentially bound to targets for binding to the poly(dT) polystyrene. The result would be diminished signals and potentially higher backgrounds as well. By presaturating the support with tailed probes, this potential competition could be minimized or eliminated along with any potential increase in background.

In Table 10, data are presented from two representative experiments comparing the results employing either the preimmobilized capture probe or the capture probe free in solution. Three situations are considered: no competitors present ($5 \times 10^6$ Campylobacter/ml only), competitor rRNA present (purified *E. coli* RNA added), or streptavidin present at 10 μg/ml. With the capture probe free in solution, there is a substantial loss of signal with competitor rRNA (34-fold decline) and streptavidin (100-fold), as predicted above.

With the preimmobilized capture probe, however, there was no loss in signal with competitor rRNA or with streptavidin. Thus this method allows us to exploit the advantages of using a single completely generic detector probe that is conveniently labeled with moieties such as biotin.

TABLE 10

Comparison of Competitor Effects on Solution and Immobilized Assay Formats

| | OD 405 nm | |
|---|---|---|
| Sample | SOLUTION | IMMOBILIZED |
| Experiment A: | | |
| Campylobacter | 1.209 | 1.044 |
| Campylobacter + *E. coli* RNA | 0.033 | 1.226 |
| Campylobacter + Streptavidin | 0.000 | 1.348 |
| Experiment B: | | |
| Campylobacter | 0.962 | 0.796 |

TABLE 10-continued

Comparison of Competitor Effects on
Solution and Immobilized Assay Formats

| Sample | OD 405 nm | |
|---|---|---|
| | SOLUTION | IMMOBILIZED |
| Campylobacter + *E. coli* RNA | 0.031 | 0.719 |
| Campylobacter + Streptavidin | 0.006 | 0.625 |

Legend: Campylobacter specific capture probe 732 (dA65) was used to assay Campylobacter extracts (5.0E6 cells/ml) in the presence of *E. coli* RNA (approx. 100 ug/ml), poly(A) (10 ug/ml), or streptavidin (10 ug/ml). Poly (dT) coated polystyrene dipsticks were used as a solid support for the capture of target molecules. Two different assay formats were used. In the first, dipsticks were added to samples along with the addition of the capture probe and the biotinylated riboprobe (both at 0.5 ug/ml) and incubated at 37 degrees for 60 minutes. The sticks were washed, incubated with a SA-AP conjugate, washed again, and then the signal was detected with pNPP. The second format used was the standard protocol with the capture probe immobilized on the dipsticks, the use of a TEA Cl wash step, and the addition of the labeled probe after the capture and TEA Cl steps. The capture step was for 60 min. and the riboprobe incubation for 30 min. A volume of 0.5 ml was used for all reagents except the 1 M NaCl wash buffer (washes done in bulk). Results are the average of duplicates.

Equivalents

Those skilled in the art will recognize, or be able to ascertain by no more than routine experimentation, many equivalents to the specific embodiments of the invention described herein. Such equivalents are intended to be encompassed by the following claims.

What is claimed is:

1. A method of determining the presence or amount of a target nucleic acid sequence in a specimen comprising the steps of:
   a) combining the specimen with a quantity of a chaotropic agent sufficient to disrupt molecular structures in cells and to render nucleic acids available for hybridization, thereby obtaining a mixture;
   b) combining the mixture obtained in (a) with a capture probe consisting essentially of:
      (i) a target binding region which is an oligonucleotide sequence complementary to the target nucleic acid sequence, and
      (ii) a tail region which is a nucleotide sequence that is one member of a nucleotide affinity pair,
      wherein the capture probe is preimmobilized by means of nucleotide affinity pair binding between the tail region of the capture probe and a complementary polynucleotide affixed to a solid polymeric support;
   c) maintaining the product of (b) under conditions sufficient for hybridization of complementary nucleotide sequences to occur, whereby if the target nucleic acid is present in the specimen, said target nucleic acid hybridizes to the target binding region of the preimmobilized capture probe. thereby producing an immobilized target nucleic acid;
   d) labeling the immobilized target nucleic acid with a detectable agent capable of selectively binding to the target nucleic acid, whereby a detectably labeled immobilized target nucleic acid is obtained; and
   e) detecting the presence or amount of the detectably labeled immobilized target nucleic acid.

2. A method of claim 1, wherein the solid polymeric support is polystyrene.

3. A method of claim 2, wherein the polystyrene support is a microtiter well, a tube or a dipstick.

4. A method of claim 1, wherein the substratum comprises a homopolynucleotide.

5. A method of claim 4, wherein the homopolynucleotide is selected from the group consisting of: poly(dT), oligo (dT), poly(da) and oligo(dA).

6. A method of claim 5, wherein the method further comprises washing
   (i) the preimmobilized capture probe of (b) prior to combining it with the mixture obtained in (a), or
   (ii) the immobilized target obtained in (c),
   with a solution of a tetraalkylammonium salt.

7. A method of claim 6, wherein the tetraalkylammonium salt is selected from the group consisting of: tetraethylammonium chloride, tetraethylammonium bromide tetramethylammonium chloride and tetramethylammonium bromide.

8. A method of claim 1, wherein the specimen is derived from bacteria or viruses.

9. A method of detecting the presence of target nucleic acid in an immobilized target complex in the presence of non-target nucleic acids wherein the immobilized target complex comprises a solid support having affixed thereto a polynucleotide that comprises one member of an A:T nucleotide affinity pair, to which is hybridized a capture probe consisting essentially of:
   (i) a tail region complementary to the affixed polynucleotide; and
   (ii) a nucleotide sequence that is complementary to a sequence of a target nucleic acid, to which in turn is hybridized said target nucleic acid;
   the method comprising:
      (a) washing the immobilized target complex with a wash buffer appropriate to lower nonspecific binding of non-target nucleic acids to the immobilized target complex, and
      (b) detecting the presence of the target nucleic acid with a labeled oligonucleotide probe consisting essentially of a detectable label and a nucleotide sequence complementary to a sequence of said target nucleic acid.

10. A method of determining the presence or amount of a target nucleic acid in a sample using a reversible target capture protocol comprising the steps of:
   a) providing a preimmobilized first capture probe consisting essentially of:
      (i) a first capture probe consisting essentially of:
         a target specific oligonucleotide, the nucleic acid sequence of which is specific for a target nucleic acid sequence, and
         (B) a short tail of from about 10 to about 30 nucleotides, wherein said short tail is hybridized to
      (ii) a first polynucleotide complementary to said short tail and affixed to a first solid polymeric support, such that a first hybridized region exists between said short tail and said first polynucleotide;
   b) contacting the preimmobilized first capture probe with the sample under conditions which are:
      (i) sufficient to allow hybridization of the target nucleic acid with the target-specific oligonucleotide of (a) (i) (A), thereby forming a second hybridized region between the target nucleic acid and said target-specific oligonucleotide, and
      (ii) sufficient to maintain stability of the first hybridized region, thereby producing a first solid phase;
   c) eluting the first solid phase with a chaotropic solvent sufficient to destabilize either the first hybridized region or the second hybridized region, whereby a released target nucleic acid is obtained;

d) combining the released target nucleic acid with a second preimmobilized capture probe consisting essentially of:
  (i) a second capture probe consisting essentially of:
    (A) a target-specific oligonucleotide, the nucleic acid sequence of which is specific for a target nucleic acid sequence, and
    (B) a long tail of from about 30 to about 100 nucleotides, wherein said long tail is hybridized to
  (ii) a second polynucelotide complementary to said long tail and affixed to a second solid polymeric support, such that a third hybridized region exists between said long tail and said second polynucleotide;

e) maintaining the combination of (d) under conditions which are:
  (i) sufficient to allow hybridization of the released target nucleic acid with the target-specific oligonucleotide of (d) (i) (A), thereby forming a fourth hybridized region between the target nucleic acid and said target-specific oligonucleotide, and
  (ii) sufficient to maintain stability of the third hybridized region, thereby producing a second solid phase;

f) labeling said target nucleic acid; and g) measuring the presence or amount of said labeled target nucleic acid associated with the second solid phase.

11. The method of claim 10, wherein the short tail is approximately 10–20 nucleotides.

12. The method of claim 10 wherein the first hybridized region comprises an A:T or an A:U affinity pair and is stabilized by adding a tetraalkylammonium salt.

13. The method of claim 10, wherein the chaotropic solvent is GuSCN.

14. The method of claim 10, wherein the nucleic acid sequence of the target-specific oligonucleotide of the second capture probe is the same as that of the first capture probe.

15. The method of claim 10, wherein the nucleic acid sequence of the target-specific oligonucleotide of the second capture probe is different from that of the first capture probe.

16. A kit comprising:
  a) solid polymeric supports, each having affixed thereto a polynucleotide to which is hybridized the tail of a capture probe comprised of a target-specific oligonucleotide and a tail complementary to the affixed polynucleotide; and
  b) a chaotropic agent sufficient to disrupt molecular structures in cells.

17. A kit of claim 16, wherein the solid polymeric supports comprise agarose beads, polystyrene microtiter wells, polystyrene tubes or polystyrene dipsticks.

18. A kit of claim 16, wherein the polynucleotide substratum comprises a homopolynucleotide.

19. A kit of claim 16, wherein the affixed polynucleotide and the capture probe tail comprise an A:T polynucleotide nucleotide affinity pair.

20. A method of determining the presence or amount of a target nucleic acid sequence in a specimen in which nucleic acids have been rendered available for hybridization, comprising the steps of:
  a) combining said specimen with a capture probe consisting essentially of:
    (i) a target binding region which is an oligonucleotide sequence complementary to the target nucleic acid sequence, and
    (ii) a tail region which is a nucleotide sequence that is one member of a nucleotide affinity pair,
      wherein the capture probe is preimmobilized by means of nucleotide affinity pair binding between the tail region of the capture probe and a complementary polynucleotide affixed to a solid polymeric support;
  b) maintaining the combined specimen and preimmobilized capture probe under conditions sufficient for hybridization of complementary nucleotide sequences to occur, whereby if the target nucleic acid is present in the specimen, said target nucleic acid hybridizes to the target binding region of the preimmobilized capture probe, thereby producing an immobilized target nucleic acid;
  c) labeling the immobilized target nucleic acid with a detectable agent capable of selectively binding to the target nucleic acid, whereby a detectably labeled immobilized target nucleic acid is obtained; and
  d) detecting the presence or amount of the detectably labeled immobilized target nucleic acid.

21. The method of claim 9 whereby in step (a) nonspecific binding between non-target nucleic acid which is nonspecifically bound to the immobilized target complex and support, and the labeled oligonucleotide probe is reduced and target-specific binding between the target nucleic acid and the labeled oligonucleotide probe is enhanced.

22. The method of claim 9 wherein the wash buffer comprises a quaternary salt.

23. The method of claim 22 wherein the quaternary salt is a tetraalkylammonium salt.

24. The method of claim 9 wherein detecting the presence of the target nucleic acid comprises contacting the washed immobilized target complex of step (a) with the labeled oligonucleotide probe.

25. The method of claim 9 wherein detecting the presence of target nucleic acid comprises dissociating the target nucleic acid from the washed immobilized target complex of step (a) and then contacting the labeled oligonucleotide probe to the target nucleic acid.

26. A method of reducing nonspecific binding of a labeled oligonucleotide probe to non-target nucleic acid which is nonspecifically bound to an immobilized target complex comprised of a solid support having affixed thereto a polynucleotide that comprises one member of an A:T nucleotide affinity pair, to which is hybridized a capture probe consisting essentially of:
  (i) a tail region complementary to the affixed polynucleotide; and
  (ii) a nucleotide sequence that is complementary to a sequence of a target nucleic acid, to which in turn is hybridized said target nucleic acid;
  the method comprising:
    a) washing the immobilized target complex with a wash buffer appropriate to lower nonspecific binding; and
    b) hybridizing the target nucleic acid with a labeled oligonucleotide probe consisting essentially of a detectable label and a nucleotide sequence complementary to a sequence of said target nucleic acid,
whereby nonspecific binding between non-target nucleic acid and the labeled oligonucleotide probe is reduced and target-specific binding between the target nucleic acid and the labeled oligonucleotide probe is enhanced.

27. The method of claim 26 wherein the wash buffer comprises a quaternary salt.

28. The method of claim 27 wherein the quaternary salt is a tetraalkylammonium salt.

29. The method of claim 26 wherein hybridizing the target nucleic acid comprises contacting the washed immobilized target complex of step (a) with the labeled oligonucleotide probe.

30. The method of claim 26 wherein hybridizing the target nucleic acid comprises dissociating the target nucleic acid from the washed immobilized target complex of step (a) and then contacting the labeled oligonucleotide probe to the target nucleic acid.

31. A method of reducing nonspecific binding of nontarget nucleic acid to an immobilized target complex comprised of a solid support having affixed thereto a polynucleotide that comprises one member of an A:T nucleotide affinity pair, to which is hybridized a capture probe consisting essentially of:

(i) a tail region complementary to the affixed polynucleotide; and (ii) a nucleotide sequence that is complementary to a sequence of a target nucleic acid, to which in turn is hybridized said target nucleic acid;

the method comprising washing the immobilized target complex with a wash buffer appropriate to lower nonspecific binding whereby nonspecific binding between the immobilized target complex and non-target nucleic acid is reduced.

32. The method of claim 31 wherein the wash buffer comprises a quaternary salt.

33. The method of claim 32 wherein the quaternary salt is a tetraalkylammonium salt.

* * * * *